United States Patent [19]

Keyworth

[11] Patent Number: 4,816,139
[45] Date of Patent: Mar. 28, 1989

[54] METHOD FOR REMOVING SULFUR COMPOUNDS FROM $C_6$ AND LOWER ALKANES

[75] Inventor: Donald A. Keyworth, Houston, Tex.

[73] Assignee: Tenneco Oil Company, Houston, Tex.

[21] Appl. No.: 204,998

[22] Filed: Jun. 10, 1988

Related U.S. Application Data

[63] Continuation of Ser. No. 879,407, Jun. 27, 1986, abandoned.

[51] Int. Cl.$^4$ .............................................. C10G 27/02
[52] U.S. Cl. .................................... 208/190; 585/803; 585/830; 585/856; 210/756
[58] Field of Search ............... 208/190; 585/803, 830, 585/856; 423/242 A; 210/756

[56] References Cited

U.S. PATENT DOCUMENTS

| | | | |
|---|---|---|---|
| 1,999,041 | 4/1935 | Dustan | 208/190 |
| 2,066,925 | 1/1937 | Yabroff et al. | 208/237 |
| 2,713,077 | 7/1955 | Rieve | 208/240 |
| 2,718,489 | 9/1955 | Coonradt et al. | 208/240 |
| 2,730,486 | 1/1956 | Coonradt et al. | 208/240 |
| 2,831,799 | 4/1958 | Coonradt et al. | 208/240 |
| 2,903,422 | 9/1954 | Van Beest et al. | 208/190 |
| 2,915,461 | 12/1954 | Davies et al. | 208/190 |
| 2,944,010 | 7/1960 | Webber | 208/190 |
| 3,039,957 | 6/1962 | Robbins et al. | 208/190 |
| 3,052,625 | 9/1962 | Gordon et al. | 208/190 |
| 3,108,948 | 10/1963 | Ring | 208/240 |
| 3,282,831 | 11/1960 | Harmon | 208/240 |
| 3,284,531 | 11/1966 | Shaw et al. | 585/830 |
| 3,325,553 | 6/1967 | Derfer | 208/190 |
| 3,387,941 | 6/1968 | Murphy | 208/217 |
| 3,655,803 | 4/1972 | Miller | 585/803 |
| 3,660,512 | 5/1972 | Hamby et al. | 585/803 |
| 3,674,680 | 7/1972 | Hoekstra et al. | 208/111 |
| 3,778,485 | 12/1973 | Prochazka | 208/190 |
| 3,867,509 | 2/1975 | Greiger et al. | 423/242 A |
| 3,873,672 | 3/1975 | Nishiba et al. | 423/242 A |
| 3,876,530 | 4/1975 | Frayer et al. | 208/210 |
| 3,898,155 | 8/1975 | Wilson | 208/216 |
| 3,983,030 | 9/1976 | Rosynek et al. | 208/253 |
| 4,136,021 | 1/1979 | Whitehurst | 208/251 R |
| 4,139,459 | 2/1979 | Costin | 210/37 R |
| 4,191,814 | 3/1980 | Amrick | 521/32 |
| 4,207,398 | 6/1980 | Riener | 521/31 |
| 4,212,729 | 7/1980 | Hensley et al. | 208/110 |
| 4,273,878 | 6/1981 | Amrick | 521/32 |
| 4,411,771 | 10/1983 | Bambrick et al. | 208/112 |
| 4,447,314 | 5/1984 | Banta | 208/89 |
| 4,601,816 | 7/1986 | Rankel | 208/190 |

FOREIGN PATENT DOCUMENTS 1062440 9/1979 Canada ........................ 423/242 A

OTHER PUBLICATIONS

Chem. Abs., 92, 202700p.
Chem. Abs., 92, 81619h.
Chem. Abs., 102, 190256h.
Chem. Abs., 89, 168128j.
Chem. Abs., 91, 93,636d.
Chem. Abs., 88, 141,056b.
Chemical Abstracts, 90, 15742a.
Chemical Abstracts, 87, 118723n.
Chemical Abstracts, 87, 11197h.
Chemical Abstracts, 102, 88, 94130j.
Chemical Abstracts, 79, 78527v.
Chemical Abstracts, 79, 147114e.
Chemical Abstracts, 79, 107945v.
Chemical Abstracts, 80, 121773q.

*Primary Examiner*—Asok Pal
*Assistant Examiner*—Helane Myers
*Attorney, Agent, or Firm*—Kenneth H. Johnson

[57] ABSTRACT

Small quantities of monosulfide organic compounds are removed from low boiling hydrocarbon fractions, e.g., n-hexane and lower by contacting the hydrocarbon stream with a dilute aqueous solution of NaOCl, which converts low boiling (n-hexane and lower range) monosulfides to high boiling sulfones allowing separation by fractionating the n-hexane through the lower boiling pentanes away. The NaOCl process does not appreciably effect disulfides, which boil at temperatures higher than Hexane, except for $CS_2$. Hence a hydrocarbon stream that also contains carbon disulfide, produces a hydrocarbon fraction sustantially free of monosulfides, but containing $CS_2$. The hydrocarbon fraction is then contacted with a quaternary ammonium cation exchange resin which removes $CS_2$ to produce a substantially sulfur free n-hexane through lower boiling pentanes cut, which is useful for isomerization to higher octane feed stock.

24 Claims, No Drawings

METHOD FOR REMOVING SULFUR COMPOUNDS FROM C₆ AND LOWER ALKANES

This application is a continuation of application Ser. No. 879,407, filed 6-27-86 now abandoned.

BACKGROUND OF THE INVENTION

1. Field of the Invention

The present invention relates to a method for reducing sulfur compounds in hydrocarbon streams.

2. Related Art

There is a vast body of art relating to the removal of sulfur compounds from hydrocarbon streams, such as the removal of sulfur compounds from oil fractions and heavy residue. Generally these procedures relate to hydrotreating the fraction at elevated temperatures and pressures usually in the presence of a solid contact material, e.g., U.S. Pat. Nos. 4,447,314; 4,411,771; 4,212,729; 3,983,030; 3,898,155; 3,876,530 and 3,674,680. These procedures are costly because of equipment requirements and catalyst as well as the requirement for relatively frequent regeneration of the catalyst.

The present invention is directed to the removal of small amounts of sulfur compounds from hydrocarbon streams to extremely low levels. The treated streams of the present invention may be final product streams or may be intended for subsequent processing where sulfur is detrimental.

The reactivity of organic sulfur compounds with various other materials has been observed. For example, sodium hypochlorite has been observed to oxidize some organic sulfur compounds, e.g., Homer, et al., "Sur Oxidation Von Thioethers mit Hypochlorit", *Phosphorus Sulfur*, 22 (1) p. 5–11 (1985), documents oxidation studies of thioethers in toluene with dilute aqueous sodium hypochlorite under a variety of pH values and hypochlorite concentrations. Other art shows MeSH, Me₂S and Me₂S₂ were removed by oxidation with NaOCl (5 ppm each) in two stages of scrubbing, at pH 7 and 11, [CA 92 202700p (1980) "Oxidative Treatment of Sulfur Compounds with Sodium Hypochlorite" Abe, et al., *Anzen Kogku* 1979, 18(5), 271–4]; odorous compounds were removed from Kraft Paper mill waste gases by scrubbing with an aqueous solution containing hypochlorite (5.5% NaOCl and 45% Na₂CO₃ pH 11.3), [CA 92 81619L (1980) "Method and Apparatus for Removing Reduced Sulfur Compounds from Vapors and/or Gas Streams" Parahacs, et al., Can 1062440 18 Sept. 1979]; waste gases from an edible oil plant were deodorized (MeSH, Me₂S and H₂S removed) with 500–1000 mg NaOCl/L solution [CA 102 190256h "Treatment of Waste Gas", Japan Kakai Tokyo, JP No. 6,007,024 (8,507,924) Jan. 16, 1985]; comparative studies showed NaOCl was the most practical scrubbing agent for reducing S emissions in flue gas in paper mills [CA 89 168128j "Removal of Organic Sulfur Compounds from Kraft Emissions Using Wet Scrubbing Techniques" Azarnionch, et al., *Prepr Pap* Annual Meeting Tech Sect CPPA, 63rd, 1977 A 179–84]; MeSH and Me₂S were treated with circulating aqueous Ca(OCl)₂ for complete removal [CA 91 93636d "Removal of Gaseous Organic Sulfur Substances" Muraoka, et al., Jpn Tokyo Koho No. 7,904,699, Mar. 9, 1979]; and a turbulent, 3-stage contact absorber removed organic S compounds from flue gas with 500–700 ppm NaOCl at a pH of 9–9.5 [CA 88 141056b "Novel Wet Scrubbing Techniques for the Removal of Hydrogen Sulfide and Organic Sulfur Compounds," Prahacs, et al., Proc Int Clean Air Cong 4th 1977; 752-S].

Another example of the reactivity of organic sulfur compounds is the reactivity of carbon disulfide with base forms of anion exchange resins which is known from work relating to detoxification of waste water, removal of acid gases from waste gases and formation of useful polydithiocarbonates heavy metal removal catalyst e.g., Chemical Abstracts 90, 15742a; 87, 118723n; 87, 11197h; 88, 94130j; 79, 78527v; 79, 147114e; 79, 107945v and 80, 121773q. The NaOCl treatment and contact with anion exchange resin are totally different processes. The former converts low boiling sulfides to high boiling materials and the latter extracts the CS₂ from the stream.

With the removal of tetraethyl lead from gasoline, straight run gasoline, which has poor BVON characteristics will not be suitable for blending into gasoline. However, by separating isoalkanes from the n-alkanes the n-alkanes can be isomerized to isoalkanes, and a good blending value material is recoverable. There is usually a small amount of sulfur in various forms present. The preferred low temperature isomerization catalysts are sulfur intolerant (1 ppm or less sulfur in feed). Hence removal of the sulfur (including CS₂) in a simple fashion is necessary to achieve a useful catalyst life.

It is an advantage of the present invention that small amounts of organic sulfur compounds may be substantially removed from hydrocarbon streams. It is a feature of the present invention that a process for such treatment is provided using very moderate treatment conditions. These and other advantages and features will become apparent from the following description.

SUMMARY OF THE INVENTION

Briefly, the present invention is a process for recovering a low sulfur content hydrocarbon fraction having a boiling point of n-hexane or less from a hydrocarbon stream containing hydrocarbons boiling at or below the boiling point of n-hexane and organic sulfur compounds particularly monosulfides boiling in the n-hexane or lower range, which comprises contacting said hydrocarbon stream in liquid phase with a dilute solution of sodium hydrochlorite, separating an aqueous phase and a hydrocarbon phase and fractionating said hydrocarbon phase to recover a hydrocarbon fraction having a boiling point of n-hexane or less and having a reduced amount of said organic sulfur compounds therein. The two phases are preferably intimately mixed in order to have a thorough contacting.

The dilute aqueous solution of NaOCl may contain from about 1 to 15 wt. % NaOCl, preferably 4 to 10 wt. % NaOCl. Generally the volume ratio of aqueous phase to hydrocarbon phase is from 0.2:1 to 10:1 and preferably 0.5:1 to 5:1. The intimate mixing may take the form of emulsions, i.e., oil in water or water in oil thus the ratio of aqueous phase to hydrocarbon phase should avoid proportions where stable emulsions are formed since phase separation is essential.

The organic sulfur compounds may be characterized as consisting of carbon and sulfur or carbon, sulfur and hydrogen. The residence time of the contacting depends somewhat on the relative amount of the aqueous phase and the concentration of the NaOCl therein and the concentration of sulfur compounds. At 1:1 ratio of aqueous phase (5.25 wt. % NaOCl) : to hydrocarbon (straight run gasoline containing 382 ppm S), at LHSV (liquid hourly space velocity) of up to 6 all of the sulfides (but not disulfides) were converted to higher boiling compounds. The residence time is that sufficient to convert the desired amount of monosulfide compounds present to compounds having boiling points above the boiling point of n-hexane, usually LHSV 1 to 10 are used. Adjustments in NaOCl concentration, ratio of water phase and hydrocarbon phase, temperature and the amount of sulfides to be reacted will effect the residence time required. Low boiling monosulfide, organic sulfur compounds found in petroleum hydrocarbon streams are oxidizable by NaOCl to produce higher boiling materials, possibly sulfones and sulfoxides, which are left behind by taking a $C_6$, preferably n-hexane, or lower boiling cut. Organic sulfur compounds which are higher boiling than n-hexane and which are also unaffected by the NaOCl treatment present no problem, since they are also left behind with the converted sulfur compounds. A compound of this type is methyl disulfide, which boils at 109° C. (Atm. press). Normal hexane has a boiling point of 69° C. at atmospheric pressure.

Carbon disulfide is also found not to be noticeably affected by the NaOCl treatment. Thus disulfides and carbon disulfide may be present in the feed but other organic sulfur compounds boiling in the specified range, specifically monosulfides will be present. However, $CS_2$ boils at 43° C. (atm press). Hence in another aspect of the present invention the process comprises contacting a hydrocarbon stream containing hydrocarbons boiling at or below the boiling point of n-hexane and organic sulfur compounds (monosulfides) boiling in the n-hexane or lower range in addition to carbon disulfide (which comprises contacting said hydrocarbon stream in liquid phase) with a dilute solution of NaOCl whereby a substantial portion of the organic sulfur compounds other than $CS_2$ are converted to compounds having boiling points higher than n-hexane, separating an aqueous phase and a hydrocarbon phase, fractionating the hydrocarbon phase to recover a hydrocarbon fraction having a boiling point of n-hexane or less and a reduced amount of said organic sulfur compounds other than $CS_2$ therein, and contacting said hydrocarbon fraction in liquid phase with a strongly basic anion exchange resin to reduce the $CS_2$.

The contact with the anion exchange resin may be carried out at atmospheric pressure, sub or super atmospheric pressure. Generally, the pressure will be sufficient to maintain the system in liquid phase. The temperature of the system during the contacting is preferably from about 35° to 75° C. with the upper limit being somewhat restricted by the thermal stability of the anion resin. The preferred range of temperature for contacting is 40° to 60° C.

The duration of the contact with the anion resin has been observed to be a significant factor since LHSV's above about 3 result in an observable decline in the effectiveness of the $CS_2$ removal. The preferred range is about 0.5 to 3 LHSV, preferably 1 to 2.5.

The hydrocarbon stream is that which will be a flowable liquid under the conditions of temperature defined above. More specifically the hydrocarbon streams generally comprise $C_4$ to $C_{20}$ hydrocarbons which may be mixtures or substantially pure cuts. Generally the total organic sulfur content of the hydrocarbon feed stream may be from 100 to 1500 ppm, with anywhere from about 10 to 100% boiling in the n-hexane or lower range. The low boilers are monosulfides, except for carbon disulfide. The amount of carbon disulfide in these feeds is usually below about 50 ppm, generally $CS_2$ is present in the range of 2 (usually 5) to 30 ppm, however the process is effective for feeds having much higher $CS_2$ concentrations.

DETAILED DESCRIPTION OF THE INVENTION AND PREFERRED EMBODIMENTS

Organic sulfur compounds are common impurities in hydrocarbon streams. For example, raw natural gasoline may contain numerous organic sulfur compounds boiling from less than 69° C. to well over 100° C. The present invention is directed to obtaining $C_6$ and lower cuts, e.g., n-hexane and lower boiling components, substantially free of organic sulfur compounds. The incentive for this is the potential detriment of sulfur (sulfur compounds) on catalyst, equipment and environment. It has been observed that the organic sulfides are quantitatively converted to higher boiling compounds by contact with sodium hypochlorite, whereas the organic disulfides are substantially unaffected by this treatment.

Among the organic sulfur compounds which may be contaminants or impurities in the hydrocarbon streams are dimethyl sulfide (DMS) (B.P. 37.3° C.), carbon disulfide ($CS_2$) (B.P. 46.3° C.), methylethyl sulfide (MES) (B.P. 66.9° C.), thiophene (B.P. 84° C.) and dimethyl disulfide (DMDS) (B.P. 109° C.). The sodium hypochlorite treatment readily converts DMS and MES to higher boiling compounds (above 69° C.), however, carbon disulfide, thiophene and DMDS are not affected by NaOCl. Since a fractionation to separate n-hexane (B.P. 69° C.) and lower boiling components from the higher boiling components of the stream is an element of the present process, the presence of unaffected higher boiling sulfur compounds, e.g., above 70°–75° C., does not present a problem. These higher boiling sulfur compounds will be left behind in the bottoms with the higher boiling NaOCl converted sulfur compounds.

After the fractionation the only organic sulfur compound detected was carbon disulfide. Preferred alkanes are the $C_5$ and $C_6$ alkanes. It has been observed that fractionation of a narrow cut such as a $C_5$ stream (e.g., derived from fractionation of a hydrocarbon stream, which contains both normal and isopentane) to remove the isopentane results in a concentration of carbon disulfide in the normal $C_5$'s and hence an enhancement of sulfur in that stream.

The NaOCl is used as a dilute aqueous solution, as described, i.e., from about 1 to 15 wt. % NaOCl, preferably 4 to 10 wt. % NaOCl. The NaOCl is unstable and under higher contact temperatures the instability may be enhanced. Small amounts of sodium hydroxide, e.g., 1 to 3 wt. % may be added to the hypochlorite solution to improve the stability of the hypochlorite, however, strongly basic (5 wt. % excess NaOH) results in a much slower oxidation rate. The decomposition of NaOCl in water produces nascent oxygen which is the major source of its oxidizing ability. Hence, the adjustment of the stability is to prevent unnecessary loss of the reagent, but not to create so stable a reagent as to be non reactive. "Neutral" sodium hypochlorite (no NaOH excess) was reacted at a rate of 46.5 meq. NaOCl/hr. with a synthetic feed containing 0.56 meq. S/hr. as sulfide, 5.7 meq. of NaOCl were consumed, presumably 0.56 went to the sulfide conversion and 5 meq. was lost when it decomposed to liberate oxygen.

The hydrocarbon feed and NaOCl may be contacted over a range of 10° to 80° C., preferably in the range of 20° to 70° C.

Thus the otherwise sulfur free hydrocarbon fraction may contain a substantial amount of $CS_2$, e.g., 5 to 30 ppm, which for specific uses is detrimental. Hence, in this aspect of the invention the further step of contacting the distilled fraction with the anion exchange resin is carried out to produce substantially sulfur free n-$C_6$ and lower hydrocarbon fraction.

The anion exchange resins useful for the present invention are in the macroreticular form which has surface areas of from 20 to 600 square meters per gram. Anion exchangers suitable for the present process include anion exchangers, which contain quaternary ammonium functional groups and which have been obtained by polymerization or copolymerization of aromatic vinyl compounds.

Quaternary ammonium (strong base) anion exchange resins containing a major amount of aromatic vinyl hydrocarbon and a minor amount of unsaturated cross-linking constituent of the aromatic poylvinyl hydrocarbon or polyfunctional unsaturated carboxylic acid types are known in the art to be produced according to processes wherein the comonomers are emulsion or suspension polymerized and the copolymers are haloalkylated and subsequently aminated with tertiary amines. For further details of processes, see U.S. Pat. Nos. 4,207,398; 3,843,566; 3,817,878; 3,549,562; 3,637,535; 3,297,648; 2,874,132; German Pat. No. 1,151,127 and Japanese Pat. No. 71,20,054. Typically, the haloalkylation reaction is performed by treating the precursor polymer with the haloalkylating agent in the presence of a Lewis acid catalyst (also known as a Friedel-Crafts catalyst) and in the presence of an organic swelling solvent. Quenching this reaction with water and subsequently aminolyzing the intermediate, haloalkylated copolymer produces the resin beads. Quaternary ammonium anion exchange resins prepared by other procedures such as disclosed in U.S. Pat. Nos. 4,139,459 and 4,273,878 may be employed also. The preferred catalyst are those which are converted to the OH$^-$ form. This is conveniently obtained by contacting the resin with a strong base such as alkali metal hydroxides.

The hydrocarbon stream may be derived from any source, e.g., crude oil straight run distillate, catalytic cracking, natural gasoline condensate from natural gas processing, crude oil steam distillation, steam cracking, such as ethylene production from aromatics, and the like. As previously described the hydrocarbon streams are generally the lighter components or derivatives of petroleum or synthetically produced oils. Preferably the hydrocarbon are $C_{10}$ and less, such as a $C_5$ stream.

Quaternary ammonium exchange resins may exhibit thermal instability in use in the present process by the loss of nitrogen. Hence, optimization of the conditions for the present process will include as considerations the catalyst life resulting from instability versus sulfur removal at a given temperature and LHSV. The presence of amine compounds in the product stream as the result of the resin degradation may be easily removed by conventional means, e.g., the use of a strong acid cation exchange resin such as Dowex MSC-1 (The Dow Chemical Company) or Amberlyst 15 (Rohm and Haas Company).

The following examples are intended to illustrate the invention and are not intended to limit the scope thereof. Percents (and PPM) are by weight unless otherwise indicated.

EXAMPLE 1

Straight run gasoline having the analysis shown in TABLES I and II was treated with 5.25% NaOCl in aqueous solution at various LHSV ratios of gasoline to aqueous solution. The gasoline and aqueous solution were each pumped separately to a mixing T where they were emulsified and passed upflow through a ½ inch diameter bed of 1 mm glass beads, 41 inches in length. The emulsion was delivered to a separator to recover the used NaOCl and the treated straight run gasoline. At LHSV up to 6 (both streams) monosulfides through the n-hexane boiling range were converted to higher boilers and only 2.5 ppm S remained as $CS_2$, in a 70° C. fraction.

The $CS_2$ removal is illustrated in an accelerated life test by treating a synthetic feed containing a high level of $CS_2$ (222 ppm S as $CS_2$) in n-pentane. The resin employed was Biorad AG-1X8 resin (Dowex SBR Anion Exchange resin $-OH$ form, the Dow Chemical Company), which is the OH form of styrene divinylbenzene, copolymer matrix with quaternary ammonium funcational groups. This resin employed was one previously used for $CS_2$ removal and regenerated as follows:

The resin was removed from the reactor and mixed with 150 cc of 3N hydrochloric acid and 100 cc of toluene. Carbon disulfide was released into the toluene layer and analysis showed substantially complete recovery for the $CS_2$ in the various feeds studied. The resin was vacuum filtered on a Buchner funnel, loaded into a buret and washed upflow with 300 cc of 3N hydrochloric acid followed by 400 cc of water followed by 300 cc of 3N sodium hydroxide, and finally another 400 cc of water. The resin volume was 92 cc (original wet form was 100 cc).

The reactor consisted of a nitrogen pressured 4 gallon feed tank on weight scales connected to a constametric pump for controlling LHSV of the feed upflow through a reactor packed with 100 cc of the wet resin. The reactor was jacketed to maintain near isothermal conditions through circulation of silicone oil heated electrically or cooled with a Neslab CFT 25 Coolflow refrigeration system as appropriate. The pressure of the reactor was controlled with a backflow regulator and the effluent was collected in a 5 gallon vented can.

The regenerated resin was loaded into the reactor and placed in service at 2.1 LHSV and 62° C. on a feed containing 222 ppm S as carbon disulfide in n-pentane. After 23 hours service producing effluent containing 0.3 ppm or less S, the $CS_2$ showed breakthrough of 1.2 ppm S. This service was continued 8 hours and then the feed was diluted with processed effluent to give a new feed containing 113 ppm S as $CS_2$. Using the 113 ppm S feed, the effluent contained 1 ppm or less S for another eight hours of service, at which time breakthrough (1.5 ppm S) occurred. This accelerated life study shows the $CS_2$ capacity for regenerated resin exceeds 22 days of service at 2 LHSV on a feed containing 15 ppm S as $CS_2$.

The Dohrmann CR1 sulfur analyzer was used to obtain total sulfur with the C-300 furnace and the C-300 microcoulometer. The sample to be analyzed is continuously metered (for 3 minutes) into a pyrolysis furnace at 800° C. The furnace is continuously purged with oxygen and helium. The sulfur in the sample is combusted to sulfur dioxide; and the concentration of sulfur dioxide is measured iodometrically by the microcoulometer.

n-Pentane is injected into the pyrolysis furnace without dilution for total sulfur levels from 1-10 ppm S. The analyzer is calibrated at the beginning of every sample set and with every two hours throughout the runs. Detection limits for the system is one ppm S wt.

Concentration of individual sulfur in the n-pentane is measured by gas chromatography using an electrolytic conductivity detector (Mode 4420) from O Corporation. This detector oxidizes the sulfur in the GC column effluent at 950° C. over a nickel catalyst in a microfurnace purged with air. The sulfur is oxidized to sulfur dioxide, collected in methanol and the changes in conductivity are measured. The detector is 10,000 times more responsive to sulfur than carbon. Carbon peaks except for major components do not produce a signal. The detector responds down to 0.1 ppm S.

EXAMPLE 2

The feedstock for this set of runs was n-pentane adulterated with 23 ppm S as dimethylsulfide (DMS), 23 ppm S as methylethyl sulfide (MES) and 19 ppm S as carbon disulfide ($CS_2$).

Using a fresh catalyst of the type described in Example 1, the effectiveness of this step for the removal of $CS_2$ is demonstrated even in the presence of small amounts of other sulfides.

The temperature pressure and LHSV conditions as well as the results for a series of runs are set out in the TABLE III. It was determined in an accelerated life study that the resin showed a $CS_2$ capacity breakthrough equivalent to 28 days of 15 ppm S as $CS_2$ and 2 LHSV service.

TABLE I

| ANALYSIS OF STRAIGHT RUN GASOLINE | | |
|---|---|---|
| Hydrocarbon Composition | Wt. % | B.P. °C. |
| $C_3$-$C_4$ | 3 | — |
| Isopentane | 21 | 27.9 |
| n-Pentane | 22 | 36.1 |
| n-Hexane | 7 | 68.7 |
| Branched Hexanes | 18 | |
| Heptanes | 17 | |
| $C_8$ and $C_8$+ | 12 | |

TABLE II

| SULFUR IN STRAIGHT RUN GASOLINE | | | |
|---|---|---|---|
| | | Wt. PPM | B.P. °C. |
| Total | Sulfur (Dohrmann) | 382 | — |
| | Dimethyl Sulfide | 15 | 37.3 |
| | Carbon Disulfide | 2-3 | 46.3 |
| | Methylethyl Sulfide | 14 | 66.9 |
| | Thiophene | 2 | 84 |
| | Dimethyl Disulfide | 16 | 109 |

TABLE III

| LHSV | °C. | PSIG | TOTAL PPM S WT. | PPM S As DMS | PPM S As MES | PPM S As $CS_2$ |
|---|---|---|---|---|---|---|
| Feed | — | — | 65 | 23 | 23 | 19 |
| 2 | 62 | 120 | 30 | 15 | 14 | 0.3 |
| 2.6 | 68 | 120 | 28 | 14 | 14 | 0.1 |
| 3.6 | 69 | 120 | 33 | 16 | 15 | 2.7 |
| 2.0 | 45 | 120 | 46 | 24 | 17 | 5.4 |
| 1.1 | 45 | 120 | 40 | 25 | 15 | 0.3 |
| 0.9 | 45 | 120 | 33 | 20 | 13 | 0.1 |
| 2 | 50 | 120 | 42 | 18 | 16 | 2 |
| 2.5 | 55 | 230 | 32 | 15 | 13 | 3.8 |

The invention claimed is:

1. A process for recovering a low sulfur content hydrocarbon fraction having a boiling point of n-hexane or less from a hydrocarbon stream containing hydrocarbons boiling at or below the boiling point of hexane and organic sulfur compounds comprising monosulfides boiling at or below the boiling point of n-hexane comprising contacting said hydrocarbon stream with a dilute aqueous solution of sodium hypochlorite for a time sufficient to convert a selected amount of monosulfide compounds present to compounds having boiling points above the boiling point of n-hexane, separating an aqueous phase and a hydrocarbon phase and fractionally distilling said hydrocarbon phase to recover a hydrocarbon fraction having a boiling point of n-hexane or less and having a reduced amount of said organic sulfur compounds.

2. A process for recovering a low sulfur content hydrocarbon fraction comprising contacting a hydrocarbon stream comprising hydrocarbons and organic sulfides including organic monosulfides boiling at or below the boiling point of n-hexane with a dilute aqueous solution of sodium hypochlorite for a time sufficient to convert a selected amount of monosulfide compounds present to compounds having boiling points above the boiling point of n-hexane, separating an aqueous phase and a hydrocarbon phase and fractionally distilling said hydrocarbon phase to recover a hydrocarbon fraction having a boiling point of n-hexane or less and having a reduced amount of said organic monosulfide.

3. The process according to claim 2 wherein from about 1 to 15 wt. % NaOCl is present in the aqueous phase.

4. The process according to claim 3 wherein from about 4 to 10 wt. % NaOCl is present in the aqueous phase.

5. The process according to claim 3 wherein the volume ratio of aqueous phase to hydrocarbon phase is from 0.2:1 to 10:1.

6. The process according to claim 5 wherein the volume ratio of aqueous phase to hydrocarbon phase is from 0.5:1 to 5:1.

7. The process according to claim 3 wherein up to 5 wt. % NaOH is present in the aqueous phase.

8. The process according to claim 7 wherein from 1 to 3 wt. % NaOH is present in the aqueous phase.

9. The process according to claim 5 wherein from 100 to 1500 ppm sulfur compounds are present in the hydrocarbon stream.

10. The process according to claim 9 wherein said sulfur copounds comprise carbon and sulfur or carbon, sulfur and hydrogen.

11. The process according to claim 10 wherein said sulfur compounds comprise dimethyl sulfide and methylethyl sulfide.

12. The process according to claim 10 wherein said sulfur compounds comprise dimethyl sulfide, methylethyl sulfide and carbon disulfide.

13. The process according to claim 10 wherein said hydrocarbon fraction is contacted with a strongly basic anion exchange resin.

14. The process according to claim 13 wherein said resin is a quaternary ammonium anion exchange resin.

15. The process according to claim 14 wherein said resin is the OH− form.

16. The process according to claim 13 wherein the LHSV of the hydrocarbon fraction contacting said resin is from 0.5 to 3.

17. The process according to claim 16 wherein said LHSV is 1 to 2.5.

18. The process according to claim 17 wherein the temperature of said contacting is in the range of 35° to 75° C.

19. The process according to claim 1 wherein said hydrocarbon phase and aqueous phase are emulsified for contact and demulsified for fractional distillation of the hydrocarbon phase.

20. A process for recovering a low sulfur content hydrocarbon fraction comprising:
intimately contacting a hydrocarbon stream comprising $C_4$ to $C_{20}$ hydrocarbons, monosulfide organic compounds and carbon disulfide with an aqueous solution of 4 to 10 wt.% NaOCl in a volume ratio of aqueous phase to hydrocarbon phase in the range of 0.5:1 to 5:1 at an Liquid Hourly Space Velocity of 1 to 10 at a temperature in the range of 40° to 60° C.;
separating the aqueous phase and the hydrocarbon phase;
fractionally distilling the hydrocarbon phase to recover a hydrocarbon fraction having a boiling point of n-hexane or less and a reduced amount of monosulfide organic compound;
contacting said hydrocarbon fraction in liquid phase with a quaternary ammonium anion exchange resin at 35° to 75° C. at an Liquid Hourly Space Velocity in the range of 0.5 to 3; and
recovering the hydrocarbon fraction with a reduced amount of carbon disulfide.

21. The process according to claim 20 wherein said monosulfide organic compounds comprise dimethyl sulfide and methylethyl sulfide.

22. The process according to claim 20 wherein said liquid hourly space velocity of the hydrocarbon fraction in the anion exchange resin is 1 to 2.5.

23. The process according to claim 22 wherein said monosulfide compounds comprise dimethyl sulfide and methyl sulfide.

24. The process according to claim 20 wherein said hydrocarbon phase and aqueous phase are emulsified for contact and demulsified for fractional distillation of the hydrocarbon phase.

* * * * *